United States Patent
Tsujino et al.

(10) Patent No.: US 6,863,883 B1
(45) Date of Patent: Mar. 8, 2005

(54) PERMANENT WAVE AGENT COMPOSITION HAVING DYEING EFFECT AND METHOD FOR DYEING HAIR USING THE SAME

(75) Inventors: Yoshio Tsujino, Osaka (JP); Takako Kamishita, Osaka (JP)

(73) Assignee: Henkel Lion Cosmetics Co. Ltd., Osaka (JP)

( * ) Notice: Subject to any disclaimer, the term of this patent is extended or adjusted under 35 U.S.C. 154(b) by 0 days.

(21) Appl. No.: 09/601,868

(22) PCT Filed: Feb. 8, 1999

(86) PCT No.: PCT/JP99/00523

§ 371 (c)(1),
(2), (4) Date: Aug. 9, 2000

(87) PCT Pub. No.: WO99/40895

PCT Pub. Date: Aug. 19, 1999

(30) Foreign Application Priority Data

Feb. 10, 1998  (JP) .......................... 10/028797

(51) Int. Cl.⁷ ................................ A61K 7/06
(52) U.S. Cl. ............... 424/71.1; 424/71.2; 132/202; 132/203; 132/204; 132/210; 8/657
(58) Field of Search ............... 424/70.1, 70.2; 132/202, 203, 204, 210; 8/657, 405, 451, 454, 540, 568, 654; 534/608, 573

(56) References Cited

U.S. PATENT DOCUMENTS 5,708,151 A    1/1998  Moeckli ................. 534/608

FOREIGN PATENT DOCUMENTS

| EP | 0714954 | 6/1996 | |
|---|---|---|---|
| JP | 55 22638 | 2/1980 | |
| JP | 8507545 | 8/1996 | |
| JP | 9151121 | 6/1997 | |
| WO | 95 01772 | 1/1995 | |
| WO | 95 15144 | 6/1995 | |
| WO | WO 97/39727 | * 10/1997 | ............ A61K/7/13 |

OTHER PUBLICATIONS

English translation of the International Publication No. WO 97/39727 A1.*

* cited by examiner

*Primary Examiner*—Margaret Einsmann
*Assistant Examiner*—Eisa Elhilo
(74) *Attorney, Agent, or Firm*—Stephen D. Harper; Glenn E. I. Murphy; Gregory M. Hill

(57) ABSTRACT

A second agent composition for permanent wave treatment having a dyeing effect and a method for dyeing the hair which has been permanently waved. More particularly, a second agent composition for permanent wave treatment comprising a cationic dye having a quaternary nitrogen atom, which is optionally delocalizable, and a —X=N— bond wherein X represents a nitrogen atom or a —CH— bond, and a method for dyeing the hair which has been subjected to a permanent wave treatment using the cationic dye.

10 Claims, No Drawings

PERMANENT WAVE AGENT COMPOSITION HAVING DYEING EFFECT AND METHOD FOR DYEING HAIR USING THE SAME

CROSS REFERENCE TO RELATED APPLICATIONS

This application is a national stage application under 35 U.S.C. § 371 of international application PCT/JP99/000523 filed on Feb. 8, 1999, the international application not being published in English. This application also claims priority under 35 U.S.C. 119 to JP 28797/1998, filed on Feb. 10, 1998.

TECHNICAL FIELD OF THE INVENTION

The present invention relates to a solution composition of a permanent waving composition having a hair dyeing effect and a method for dyeing hair using the same.

BACKGROUND OF THE INVENTION

In general, a permanent waving composition comprises a first solution (reducing agent) containing thioglycolic acid and the like as a main ingredient, and a second solution (oxidative fixing agent) containing hydrogen peroxide, potassium bromate, sodium bromate and the like as a main ingredient, but, hitherto, there has not been found any permanent waving composition to which a hair dyeing effect is imparted.

Under these circumstances, a first object of the present invention is to provide a permanent waving composition to which a hair dyeing effect is imparted and which is excellent in stability, dyeability and fastness.

A second object of the present invention is to provide a method for dyeing hair comprising dyeing the hair, which has been permanently waved, with the composition as described above.

DISCLOSURE OF THE INVENTION

In order to obtain a permanent waving composition to which a hair dyeing effect is imparted, the present inventors added to a second solution of a permanent waving composition various dyes including an acidic dye and a tar-series pigment which has been conventionally used in general as a dye for a hair dye, and studied their stability, dyeability and fastness to light or to hydrolysis (hereinafter, simply referred to as "fastness"). As the result, it was found that certain cationic dyes which are proposed to be a suitable dye for a hair dye in recent years (EP 714954A, WO 95/01772 and WO 95/15144 (JP-A 8-507545)) have the most excellent stability, dyeability and fastness. Also, it was found that, when said cationic dye is used to dye hair, which has been permanently waved, the hair can be dyed with high dyeability, without deteriorating the effect of permanent waving.

That is, the present invention was completed based on such the inventor's novel findings and, in the first embodiment thereof, there is provided a second solution composition of a permanent waving composition comprising a cationic dye having a quaternary nitrogen atom which may optionally be delocalizable and a —X=N— bond, wherein X means a nitrogen atom or —CH—.

According to the first embodiment of the present invention, a second solution of a permanent waving composition having high dyeing and dyeing-fastness effect can be provided.

Moreover, in the second embodiment, the present invention provides a method for dyeing hair comprising dyeing hair, which has been permanently waved, with a composition comprising a cationic dye having a quaternary nitrogen atom which may optionally be delocalizable and a —X=N— bond, wherein X means a nitrogen atom or —CH—.

According to the second embodiment of the present invention, there is provided a method for dyeing hair which exerts high dyeing effect and dyeing-fastness, without deteriorating the effect of permanent waving.

The present invention will be illustrated below in more detail by way of the first and second embodiments in this order.

[First Embodiment]

The second solution of the permanent waving composition according to the first embodiment of the present invention is one in which the cationic dye as described above is incorporated into or combined with a conventional second solution of the permanent waving composition.

As the cationic dye to be used in the first embodiment of the present invention, there is a cationic dye represented by the formula (I):

$$[A—Z=N—B]^+X^- \quad (I)$$

wherein Z means a nitrogen atom or —CH—; A and B mean an aromatic benzene ring or heterocycle which may be optionally substituted with one or more of halogen atoms or one or more of $NR_1R_2$ or $OR_1$ groups; wherein $R_1$ and $R_2$ are the same or different and independently mean hydrogen, $C_{1-8}$ alkyl, $C_{1-4}$ hydroxyalkyl or phenyl; and $X^-$ means an anion. This cationic dye is described in detail in the above-described EP 714954A, WO 95/01772 and WO 95/15144 (JP-A 8-507545).

As a preferred anion, there are chloride, methylsulfate and the like.

Representative examples of the cationic dye are:

4-aminophenylazo-2-hydroxy-7-trimethyl ammoniumnaphthalene chloride represented by the formula (1):

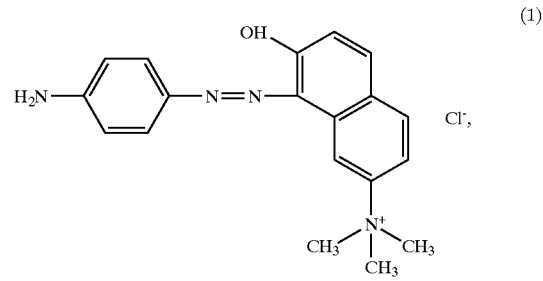

2-methoxyphenylazo-2-hydroxy-7-trimethylammoniumnaphthalene chloride represented by the formula (2):

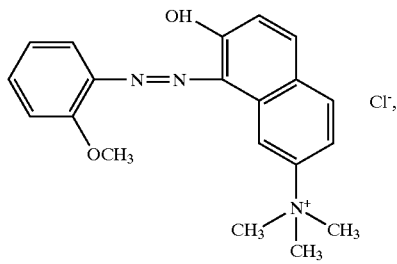

4-amino-3-nitrophenylazo-2-hydroxy-7-trimethylammoniumnaphthalene chloride represented by the formula (3):

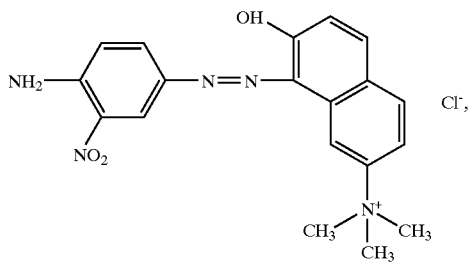

3-trimethylammoniumphenylazo-4N-phenyl-2-methyl-5-hydroxypyrazole chloride represented by the formula (4):

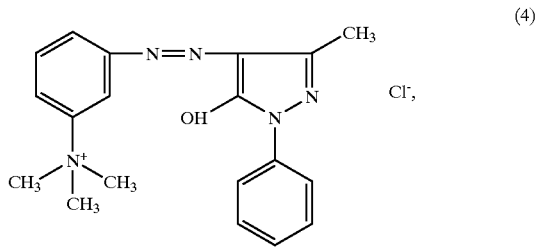

(1-methyl-1-phenyl)$_2$-(1-methine-4N-methylpyridinium) hydrazine chloride represented by the formula (5):

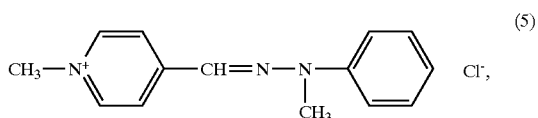

(1-methyl-1-paramethoxyphenyl)2-(1-methine-methylpyridinium)hydrazine chloride represented by the formula (6)

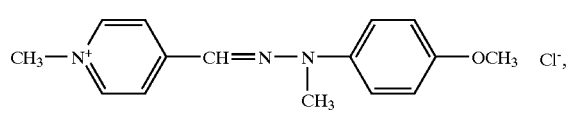

(1-methyl-1-paramethoxyphenyl)-2(1-methine-4N-methylpyridinium)hydrazine methyl sulfate represented by the formula (7):

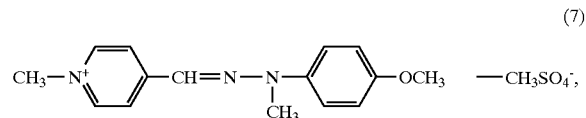

4-dimethylaminophenylazo-2N-methyl-S5-methylimidazolium chloride represented by the formula (8)

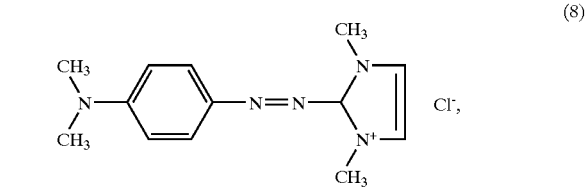

4-dimethylaminophenylazo-2N-methyl-5N-methylpyrazolium chloride represented by the formula (9):

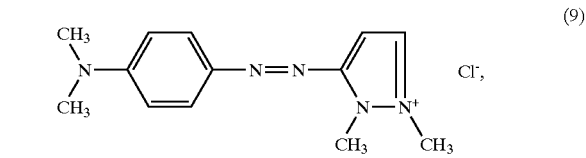

4-dimethylaminophenylazo-2N-methyl-5N-methylimidazolium chloride represented by the, formula (10):

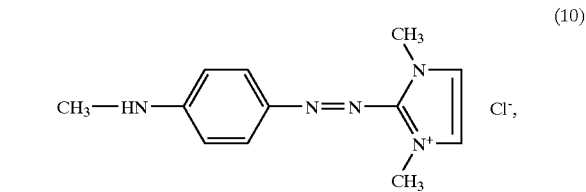

4-aminophenylazo-2N-methyl-5N-methylimidazolium chloride represented by the formula (11):

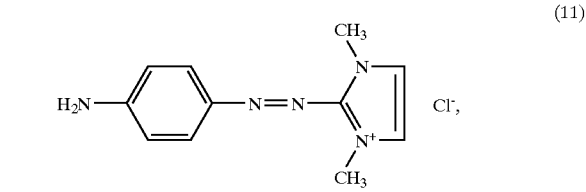

4-dimethylaminophenylazo-4N-methylpyridinium chloride represented by the formula (12):

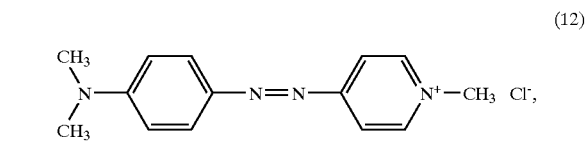

and 4-dimethylaminophenylazo-4N-oxidopyridinium chloride represented by the formula (13):

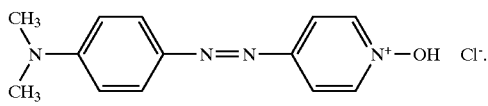

(13)

The above cationic dyes may be used alone or in a combination with two or more thereof, and an amount thereof may be optionally selected depending on the desired color but, usually, it is contained at 0.001–3% by weight based on the total amount of the second solution.

The second solution of the permanent waving composition according to the first embodiment of the present invention may be formulated into an ordinary form according to such the conventional method as mixing the desired ingredients, and the cationic dye as described above and an oxidizing agent as an essential ingredient of the second solution such as hydrogen peroxide, potassium bromate, sodium bromate, sodium perborate and the mixture thereof may be contained therein. Additionally, known ingredients which are usually used such as suitable solubilizing agents, permeating agents, lubricants, hair restorers, emulsifying agents, and perfumes may be optionally contained in the second solution. Alternatively, the dye and the oxidative fixing solution may be prepared into separate compositions to form a two-packages composition and the separate compositions may be mixed upon application.

The second solution of the permanent waving composition according to the first embodiment of the present invention may be used in the same manner as that of the known second solution and, in the case of the two-packages composition, the separate compositions may be mixed upon application.

[The second Embodiment]

The method for dyeing hair according to the second embodiment of the present invention can be conducted by dyeing the hair, which has been permanently waved, with the composition as described above.

In the case of the two-packages composition, as a dye composition to be used, an aqueous solution containing 0.001–3% by weight of a cationic dye is preferable. Particularly, an aqueous solution containing water preferably at an amount of not less than 60% by weight, more preferably not less than 80% by weight, which is adjusted to not less than pH 5, preferably pH 5–10 is preferable. For example, the hair dyeing may be conducted by permanently waving the hair with the first solution and the second solution not containing the dye, applying the composition containing the cationic dye to the hair, allowing the hair to stand for a suitable time, for example, for 2–30 minutes, adequately washing and drying. Thus, the hair can be dyed with high dyeability and fastness, without deteriorating the effect of permanent waving.

BEST MODE FOR CARRYING OUT THE INVENTION

Although the present invention will be illustrated in more detail by way of Test Examples and Examples, the present invention is not intended to be limited to them. Furthermore, hereinafter, "%" means "% by weight" unless otherwise indicated.

TEST EXAMPLE 1

Stability of a Second Solution of a Permanent Waving Composition Containing a Direct Dye with Time Each of an acidic dye, tar-series pigment and cationic dye which are a direct dye was weighed out so as to be 0.2% by weight in terms of the active ingredient, and added to a second solution of a permanent waving composition formulated as shown in Table 1 to stir.

As the acidic dye. BLACK 401, PURPLE 401 and ORANGE 205 were used. In the tar-series pigment, HC BLUE 2 and HC YELLOW 2 (manufactured by JAMS ROBINSON Inc.) were used. And, as the catatonic dye, (A): (1-methyl-1-paramethoxyphenyl)-2-(1-methane-4N-methylpyridinium)hydrazine chloride, (B): 4-dimethylaminophenylazo-2N— methyl-5N-methylimidazolium chloride and (C): 4-aminophenylazo-2N-methyl-5N-methylimidazo ium chloride (manufactured by Ciba Specialty Chemicals, Inc.) were used.

TABLE 1

| Ingredient | Amount (%) |
| --- | --- |
| Sodium bromate | 8.50 |
| Trisodium phosphate | 0.27 |
| Phosphoric acid | 0.09 |
| Purified water | Balance |

After stirring for approximately 10 minutes at room temperature, the second solution of the permanent waving composition containing the dye was filtered through a filter (TOYO ADVANTEC No. 2, circle size: 125 mm) to prepare a sample. The sample was stored at 45° C., and stability of the sample with time was evaluated for solubility of the dye in the sample, pH, absorption spectra in a visible light range.

The evaluation for solubility of the dye was conducted based on the following criteria:

○: No change in solubility compared to that measured two weeks before; and

X: Precipitation of the dye

A pH was measured with a pH meter manufactured by HORIBA Inc. Limited. Moreover, the evaluation for the absorption spectra in the visible light range was conducted by measuring an absorbance at the maximum absorbance wavelength in the absorption spectra in the visible light range using HITACHI U-3210 (using a quartz cuvette having 10 mm optical path) and calculating a ratio of the dye that remains solubilized after 4 weeks by defining the initial measured solubilized value as 100%.

The results are shown in Table 2.

TABLE 2

| | BLACK 401 | PURPLE 401 | ORANGE 205 | HC BLUE 2 | HC YELLOW 2 | Cationic Dyes | | |
| --- | --- | --- | --- | --- | --- | --- | --- | --- |
| | | | | | | (A) | (B) | (C) |
| Solubility of dye (45° C.) | | | | | | | | |
| 2 weeks | X | X | X | ○ | ○ | ○ | ○ | ○ |
| 4 weeks | ○ | ○ | ○ | ○ | ○ | ○ | ○ | ○ |

TABLE 2-continued

|  | BLACK 401 | PURPLE 401 | ORANGE 205 | HC BLUE 2 | HC YELLOW 2 | Cationic Dyes (A) | (B) | (C) |
|---|---|---|---|---|---|---|---|---|
| pH (45° C.) | | | | | | | | |
| Initial | 6.43 | 6.54 | 6.44 | 6.43 | 6.43 | 6.43 | 6.42 | 6.41 |
| 2 weeks | 6.44 | 6.52 | 6.43 | 6.44 | 6.42 | 6.42 | 6.41 | 6.40 |
| 4 weeks | 6.45 | 6.54 | 6.45 | 6.15 | 6.44 | 6.42 | 6.43 | 6.41 |
| Ratio of dye that remains solubilized after 4 weeks at 45° C. | 87.0 | 92.2 | 98.7 | 0.00 | 97.6 | 99.6 98.0 | | 102.0 |

As shown in Table 2, it was found that the dye which is stable with time in the second solution of the permanent waving composition containing the dye is the cationic dyes and the tar-series pigment HC YELLOW 2.

TEST EXAMPLE 2
Dyeability and Fastness Tests of a Second Solution of a Permanent Waving Composition Containing a Dye To approximately 2 g of goat hair, approximately 2 g of a first solution of a permanent waving composition was applied, and the hair was allowed to stand in a constant temperature bath at 30° C. for 15 minutes. Then, approximately 2 g of the same filtered second solution of a permanent waving composition as that described in Test Example 1 was applied to the hair, and the hair was shampooed and treated with a hair rinse conditioner, and adequately rinsed with water. After drying the hair, dyeability for the hair was evaluated.

Thereafter, the hair which was dyed in the dyeability test was allowed to stand for 24 hours after dyeing, then immersed into 300 ml of an aqueous solution containing 0.03/sodium polyoxyethylene (2 E.O.) alkyl (12, 13) ether sulfate at 80° C. for 10 minutes. Then, the hair was adequately rinsed with warm water, dried, and fastness was evaluated by observing dyeability for the hair after the test. The evaluation was conducted based on the following criteria:

⊚: Deeply dyed and an original white color of the goat hair is not prominent

◯: Dyed to a degree that an original white color of the goat hair is not prominent Δ: Dyed, but prominent in an original white color of the goat hair X: Only an original white color of the goat hair.
The results are shown in Table 3.

TABLE 3

| Dye | Dyeability | Fastness |
|---|---|---|
| BLACK 401 | ◯ | X |
| PURPLE 401 | X | X |
| ORANGE 205 | Δ | X |
| HC BLUE 2 | ◯ | X |
| HC YELLOW 2 | ◯ | X |
| Cationic dyes | | |
| (A) | ⊚ | ⊚ |
| (B) | ⊚ | ⊚ |
| (C) | ⊚ | ⊚ |

As shown in Table 3, the cationic dyes show excellent dyeability and fastness.

TEST EXAMPLE 3
Measurement of the Wave Index and Wave Retention Ratio of Hair Which is Dyed with a Second Solution of a Permanent Waving Composition Containing a Cationic Dye, and of Hair, which has Been Permanently Waved and, Thereafter, Dyed with an Aqueous Solution of a Cationic Dye The wave index was evaluated using human hair according to a Kirby method.

In the case of dyeing with a second solution of a permanent waving composition containing a cationic dye, the hair was immersed into each 50 g of a first solution and a second solution in this order to treat at a treatment temperature of 30° C. for a treatment period of 15 minutes. In this test, the second solution of the permanent waving composition containing 0.05% cationic dye (B) as described above was used and, after treating with the second solution, the hair was washed with water and removed from an implement, and the wave index was measured.

In the case of dyeing the hair which has permanently waved, the hair was permanently waved with the first solution and the second solution not containing the dye according to the same manner as that described above, and after treating with the second solution, the hair was adequately washed with water and immersed into a 0.05% aqueous solution of the cationic dye (B) which had been adjusted to pH 9. After treated at a treatment temperature of 30° C. for a treatment period of 30 minutes. The hair was adequately washed with water, removed from the implement and the wave index was measured.

For the wave retention rate, the hair after measuring the wave index was immersed into a 20% aqueous solution of sodium laurylsulfate at 60° C. for 20 minutes to perform a severe test, the wave index was measured according to the same manner as that described above, and a ratio of the wave index of the hair after the sever test to that before the severe test was calculated and compared.

As a control, the severe test was performed on the hair treated with the first solution and the second solution not containing the dye according to the same manner, and the wave indexes before and after the test were measured and a wave retention rate of the hair was calculated.

The results are shown in Table 4

TABLE 4

|  | Hair dyed with a second solution containing a cationic dye | Hair dyed with an aqueous solution of a cationic dye after permanent waving | Hair treated with only permanent waving |
|---|---|---|---|
| Wave index (%) | 75.32 | 74.81 | 74.34 |
| Wave retention rate (%) | 74.79 | 68.39 | 73.16 |

As shown in Table 4, the cationic dye does not deteriorate the effect of permanent waving.

TEST EXAMPLE 4
Dyeability of a Second Solution of a Permanent Waving Composition Containing a Cationic Dye and of a Cationic Dye Solution for the Permanently Waved Hair To approximately 2 g of goat hair, each 2 g of a first solution and a second solution containing 0.05% of a cationic dye (B) was applied in this order, and the hair was allowed to stand in a constant temperature bath at 30° C. for 15 minutes. After the treatment with the second solution, the hair was shampooed, treated with a hair rinse conditioner, adequately rinsed with water and dried, and dyeability was evaluated.

Thereafter, each 2 g of the first solution and the second solution not containing the dye was applied to the permanently waved hair under the same condition as that described above. After the treatment with the second solution, the hair was adequately washed with water, and 2 g of a 0.05/ aqueous solution of the cationic dye (B) which had been adjusted to pH 9 was applied to the hair which had been permanently waved and the untreated hair, respectively, which were allowed to stand at a treatment temperature of 30° C. for a treatment period of 30 minutes. Then, the hair was shampooed and treated with a hair rinse conditioner, adequately rinsed with water and dried, and dyeability was evaluated. Dyeability was evaluated according to a brightness of JIS standard color chart. The smaller value thereof indicates higher dyeability.

The results are shown in Table 5.

TABLE 5

| Dyeing condition | Hair dyed with a second solution containing a cationic dye | Hair dyed with an aqueous solution of a cationic dye after permanent waving | Untreated hair dyed with an aqueous solution of a cationic dye |
|---|---|---|---|
| Dyeability | 4 | 3.5 | 5 |

As shown in Table 5, dyeability is enhanced by permanent waving.

TEST EXAMPLE 5
Effect of a pH of a Cationic Dye on Dyeability

A 0.05% aqueous solution of a cationic dye (C) was adjusted to pH 3, 5, 7, 9 or 11, and 4 g thereof was applied to approximately 2 g of goat hair. The, hair was allowed to stand in a constant temperature bath at 30° C. for 30 minutes. Then, the hair was shampooed and treated with a hair rinse conditioner, adequately washed with water and dried, and dyeability was evaluated according to the same manner as that described in Test Example 4.

The results are shown in Table 6.

TABLE 6

| pH | 3 | 5 | 7 | 9 | 11 |
|---|---|---|---|---|---|
| Dyeability | 6.5 | 6.0 | 5.7 | 5.3 | 5.0 |

As shown in Table 6, as a pH of the aqueous solution of the cationic dye grows higher, dyeability is enhanced. But, since a solution having a pH of not less than 10 is strongly irritative to the human body and, therefore, not suitable for use, the solution may be preferably adjusted to a pH of not less than 5 and more preferably to a pH of 9. Since, in general, a second solution of a permanent waving composition is adjusted to pH 4–10.5 and, more frequently to pH 6–8, it can be expected that the second solution of the permanent waving composition exerts high dyeability even when a cationic dye is added to the permanent waving composition. Furthermore, untreated goat hair was dyed in this test, but it is predicted that the hair which has been permanently waved shows a similar tendency of dyeability depending on the pH to that of the untreated hair, though rs it merely shows a higher degree of dyeability than that of the untreated hair.

TEST EXAMPLE 6
Effect of Water Content in an Aqueous Dye Solution on Dyeability of a Cationic Dye 0.05% aqueous solutions of a cationic dye (C), each containing 0, 10, 20, 30, 40 and 50% propylene glycol respectively, were adjusted to pH 9.4 g of each solution was applied to approximately 2 g of goat hair, and the goat hair was allowed to stand in a constant temperature bath at 30° C. for 30 minutes. Then, the hair was shampooed and treated with a hair rinse conditioner, and adequately washed with water and dyeability was evaluated according to the same manner as that described in Test Example 4.

The results are shown in Table 7.

TABLE 7

| Propylene glycol wt % | 0 | 10 | 20 | 30 | 40 | 50 |
|---|---|---|---|---|---|---|
| Dyeability | 6.5 | 6.8 | 7.0 | 7.7 | 8.5 | 9.0 |

As shown in Table 7, since dyeability is considerably lowered by inclusion of propylene glycol of not less than 30%, particularly of 40 and 50% in the solution, the water content is preferably not less than 70%, more preferably not less than 80%.

EXAMPLE 1
A Second Solution Composition of a Permanent Waving Composition Utilizing Hydrogen Peroxide A second solution composition of the following formulation was prepared according to the conventional method.

| Ingredient | % |
|---|---|
| (1-methyl-1-phenyl)-2-(1-methine-4N-methylpyridinium) hydrazine methylsulfate | 0.2 |
| Hydrogen peroxide (35%) | 4.3 |
| Cetanol | 0.5 |
| Reduced lanolin | 0.35 |
| Acetanilide | 0.02 |
| Sodium pyrophosphate | 0.025 |
| Phosphotic acid, purified water (A pH was adjusted to 6.5 with phosphoric acid) | Balance |

The formulation of a first solution used was as follows.

| Ingredient | % |
|---|---|
| Ammonium thioglycolate solution (50% as thioglycolic acid) | 13.6 |
| Ammonium bicarbonate | 3.5 |
| Disodium editate | 0.1 |
| Monoethanolamine, purified water (A pH was adjusted to 9.0 with monoethanolamine) | Balance |

The permanent waving and dyeing treatment of the hair were performed as follows. According to the conventional method, a tip of the white hair was protected with paper, then the hair was wound to a plastic rod having a 1.5 cm diameter, immersed into the first solution as described above at 30° C. for 15 minutes, and washed with running water for 1 minute. Thereafter, the hair was immersed into the second solution at 30° C. for 15 minutes, washed with water, and shampooed. As the result, the white hair was imparted with a uniform wave from the root to the tip, and dyed in yellow color.

EXAMPLE 2

A Second Solution Composition of a Permanent Waving Composition Utilizing Potassium Bromate A second solution composition of the following formulation was prepared according to the conventional method.

| Ingredient | % |
| --- | --- |
| 4-dimethylaminophenylazo-2N-methyl-5N-methylimidazolium chloride | 0.2 |
| Potassium bromate | 10.2 |
| Lauryldimethyl acetate betaine | 1.0 |
| Cetyltrimethylammonium chloride | 0.6 |
| Sodium benzoate | 0.3 |
| Salicylic acid | 0.05 |
| Trisodium phosphate | 0.27 |
| Phosphoric acid, purified water | Balance |
| (A pH was adjusted to 6.5 with phosphoric acid) | |

The formulation of a first solution used was as follows.

| Ingredient | % |
| --- | --- |
| L-cysteine hydrochloride | 7.0 |
| Cetanol | 0.5 |
| Oleyl alcohol | 0.5 |
| Polyoxyethylene cetyl ether (10 E.O.) | 1.0 |
| Polyoxyethylene cetyl ether (15 E.O.) | 1.0 |
| Disodium editate | 0.1 |
| Monoethanolamine, purified water | Balance |
| (A pH was adjusted to 9.0 with monoethanolamine) | |

The permanent waving and dyeing treatment of the hair were performed using the first and second solution as described above according to the same manner as that described in Example 1. As the result, the white hair was imparted with a uniform wave from the root, and dyed in red color.

EXAMPLE 3

A Second Solution Composition of a Permanent Waving Composition Utilizing an Enzyme A second solution composition of the following formulation was prepared according to the conventional method. Uncase was added just before the treatment with the second solution.

| Ingredient | % |
| --- | --- |
| 4-aminophenylazo-2N-methyl-5N-methylimidazolium chloride | 0.2 |
| Uricase (20 units/mg) | 1.0 |
| Uric acid | 1.0 |
| Glycerol | 3.0 |
| Purified Water | Balance |

The formulation of a first solution used was as follows.

| Ingredient | % |
| --- | --- |
| Ammonium thioglycolate solution (50% as thioglycolic acid) | 13.0 |
| Polyoxyethylene cetyl ether (10 E.O.) | 1.0 |
| Polyoxyethylene cetyl ether (20 E.O.) | 1.0 |
| Sodium laurylsulfate | 0.5 |
| Hydrolyzed collagen solution | 0.4 |
| Disodium editate | 0.1 |
| Aqueous ammonia, purified water | Balance |
| (A pH was adjusted to 9.0 with aqueous ammonia) | |

The permanent waving and dyeing treatment of the hair were performed according to the same manner as that described in Example 1. As the result, the white hair was imparted with a uniform wave from the root to the tip, and dyed in orange color.

EXAMPLE 4

A Second Solution Composition of a Permanent Waving Composition Utilizing Sodium Bromate A two-packages composition consisting of an oxidative fixing solution and an dye solution of the following formulation was prepared according to the conventional method.

Oxidative Fixing Solution

| Ingredient | % |
| --- | --- |
| Sodium bromate | 17.0 |
| Lauryldimethyl acetate betaine | 1.5 |
| Cetyltrimethylammonium chloride | 1.0 |
| Sodium benzoate | 0.6 |
| Salicylic acid | 0.1 |
| Trisodium phosphate | 0.54 |
| Phosphoric acid, purified water | Balance |
| (A pH was adjusted to 6.5 with phosphoric acid) | |

Dye solution

| Ingredient | % |
| --- | --- |
| 4-(4-aminophenylamino)phenylazo-2N-methyl-5N-methylimidazolium chloride | 0.4 |
| Monoethanolamine, purified water | Balance |
| (A pH was adjusted to 8.0 with monoethanolamin) | |

The same first solution as that described in Example 3 was used.

The permanent waving and dyeing treatment of the hair were performed according to the same manner as that described in Example 1, except that an oxidative fixing solution and a dye solution were mixed in a ratio of 1:1 upon application. As the result, the white hair was imparted with a uniform wave from the root, and dyed in purple color.

EXAMPLE 5

A Second Solution Composition of a Permanent Waving Composition Utilizing Sodium Bromate A two-packages composition consisting of an oxidative fixing solution and a dye solution of the following formulation was prepared according to the conventional method.

Oxidative Fixing Solution

| Ingredient | % |
|---|---|
| Sodium bromate | 8.5 |
| Lauryldimethyl acetate betaine | 1.0 |
| Cetyltrimethylammonium chloride | 0.6 |
| Sodium benzoate | 0.3 |
| Salicylic acid | 0.05 |
| Trisodium phophate | 0.27 |
| Phosphoric acid, purified water | Balance |
| (A pH was adjusted to 6.5 with phosphoric acid) | |

Dye Powder

| Ingredient | % |
|---|---|
| (1-methyl-1-paramethoxyphenyl)-2-(1-methine-4N-methylpyridinium) hydrazine chloride (to the oxidative fixing solution) | 0.02 |
| 3-amino-7-(dimethylamino)-2-methoxyphenoxazine-5-ium chloride (to the oxidative fixing solution) | 0.02 |

The same first solution as that described in Example 3 was used.

The permanent waving and dyeing treatment of the hair were conducted according to the same manner as that described in Example 1, except that an oxidative fixing solution and dye powder were mixed in a ratio of 10:1 upon co application. As the result, the white hair was imparted with a uniform wave from the root, and dyed in green color.

EXAMPLE 6

Method for Dyeing Hair which has Been Permanently Waved

A dye solution of the following formulation was prepared.

| Ingredient | % |
|---|---|
| (1-methyl-1-paramethoxyphenyl)-2-(1-methine-4N-methylpyridinium) hydrazine chloride | 0.02 |
| hydroxyethyl cellulose | 2.5 |
| Triethanolamine, purified water | Balance |
| (A pH was adjusted to 8.0 with triethanolamine) | |

The same oxidative fixing solution as that described in Example 5 and the same first solution as that described in Example 3 were used.

The permanent waving of hair was performed using a first solution and an oxidative fixing solution according to the same manner as that described in Example 1. Thereafter, the dye solution was applied to the white hair, and the white hair was allowed to stand at 30° C. for 30 minutes, washed with water, shampooed and dried. As the result, the white hair was imparted with a uniform wave from the root to the tip, and dyed in yellow color.

INDUSTRIAL APPLICABILITY

According to the present invention, by incorporating or combining certain cationic dyes into or with a conventional second solution composition of a permanent waving composition, there is provided a second solution composition of a permanent waving composition which is excellent in stability, dyeability and fastness. In addition, according to the present invention, by dyeing with the above composition, hair which has been permanently waved can be dyed with high dyeability and fastness, without deteriorating the effect of permanent waving.

What is claimed:

1. A two-package kit for permanently waving hair comprising:

(a) a cationic dye solution comprising at least one cationic dye, wherein the cationic dye is present in an amount effective to color hair and has a quaternary nitrogen atom that is optionally delocalizable and an —X=N— bond, wherein X is a nitrogen atom or an —CH— group;

(b) an oxidative fixing solution comprising at least one oxidative fixing agent for permanently waving the hair; and (c) a reducing composition comprising at least one reducing agent in a sufficient amount for waving hair.

2. The kit of claim 1, wherein the cationic dye is represented by formula I:

$$[A—Z=N—B]^+X^- \quad \text{(II)}$$

wherein Z is a nitrogen atom or a CH group;

A and B are independently of one another, a benzene ring or aromatic heterocycle group that is substituted or unsubstituted; and $X^-$ is an anion.

3. The kit of claim 1, wherein the cationic dye comprises 4-aminophenylazo-2-hydroxy-7-trimethylammoniumnaphthalene chloride, 2-methoxyphenylazo-2-hydroxy-7-trimethylammoniumnaphthalene chloride, 4-amino-3-nitrophenylazo-2-hydroxy-7-trimethylammoniumnaphthalenechloride, 3-trimethylammoniumphenylazo-4N-phenyl-2-methyl-5-hydroxypyrazole chloride, (1-methyl-1-phenyl)-2-(1-methine-4N-methylpyridinium) hydrazine chloride, (1-methyl-1-paramethoxyphenyl)-2-(1-methine-4N-methylpyridinium) hydrazine chloride, (1-methyl-1-paramethoxyphenyl)-2-(1-methine-4N-methylpyridinium) hydrazine methylsulfate, 4-dimethylaminophenylazo-2N-methyl-5N-methylimidazolium chloride, 4-dimethylaminophenylazo-2N-methyl-3N-methylpyrazolium chloride, 4-methylaminophenylazo-2N-methyl-5N-methylimidazolium chloride, 4-aminophenylazo-2N-methyl-5N-methylimidazolium chloride, 4-dimethylaminophenylazo-4N-methylpyridinium chloride, 4-dimethylaminophenylazo-4N-oxidopyridinium chloride, 4-(4-aminophenylamino) phenylazo-2N-methyl-5N-methylimidazolium, or 3-amino-7-(dimethylamino)-2-methoxyphenoxazine-5-ium chloride, or combinations thereof.

4. A method of permanently waving hair comprising (a) applying a reducing solution to hair wherein the reducing solution comprises at least one reducing agent in a sufficient amount for waving hair;

(b) applying at least one oxidative fixing solution to the hair wherein the oxidative fixing solution comprises at least one oxidative fixing agent for permanently waving the hair; and (c) applying to the hair at least one cationic dye in an amount effective to color the hair and having a quaternary nitrogen atom that is optionally delocalizable and an —X=N— bond, wherein X is a nitrogen atom or a —CH— group, and wherein the catatonic dye is applied to the hair as a component of the oxidative fixing solution.

5. The method of claim 4, wherein the cationic dye is represented by formula I:

 (I)

wherein Z is a nitrogen atom or a CH group;

A and B are independently of one another, a benzene ring or aromatic heterocycle group that is substituted or unsubstituted; and $X^-$ is an anion.

6. The method of claim 5, wherein A or B or both have one or more substituents selected from halogen atoms, $NR_1R_3$ groups, or $OR_1$ groups, wherein $R_1$ and $R_2$ are independently selected from hydrogen, a $C_1$ to $C_6$ alkyl group, a $C_1$ to $C_4$ hydroxyalkyl group, or a phenyl group.

7. The method of claim 6, wherein the cationic dye comprises 4-aminophenylazo-2-hydroxy-7-trimethylammoniumnaphthalene chloride, 2-methoxyphenylazo-2-hydroxy-7-trimethylammoniumnaphthalene chloride, 4-amino-3-nitrophenylazo-2-hydroxy-7-trimethylammoniumnaphthalenechloride, 3-trimethylammoniumphenylazo-4N-phenyl-2-methyl-5-hydroxypyrazole chloride, (1-methyl-1-phenyl)-2-(1-methine-4N-methylpyridinium) hydrazine chloride, (1-methyl-1-paramethoxyphenyl)-2-(1-methine-4N-methylpyridinium) hydrazine chloride, (1-methyl-1-paramethoxyphenyl)-2-(1-methine-4N-methylpyridinium) hydrazine methylsulfate, 4-dimethylaminophenylazo-2N-methyl-5N-methylimidazolium chloride, 4-dimethylaminophenylazo-2N-methyl-3N-methylpyrazolium chloride, 4-methylaminophenylazo-2N-methyl-5N-methylimidazolium chloride, 4-aminophenylazo-2N-methyl-5N-methylimidazolium chloride, 4-dimethylaminophenylazo-4N-methylpyridinium chloride, 4-dimethylaminophenylazo-4N-oxidopyridinium chloride, 4-(4-aminophenylamino)phenylazo-2N-methyl-5N-methylimidazolium, or 3-amino-7-(dimethylamino)-2-methoxyphenoxazine-5-ium chloride, or combinations thereof.

8. The method of claim 4, wherein the catatonic dye is present in the oxidative fixing solution in an amount of from 0.001 weight percent to 3 weight percent, based on the total weight of the solution.

9. The method of claim 4, wherein the solution containing the cationic dye has a pH of 5 or greater.

10. The method of claim 9, wherein the solution containing the cationic dye comprises 60 weight percent or greater water.

* * * * *